United States Patent [19]

Inoue et al.

[11] Patent Number: 5,985,882
[45] Date of Patent: Nov. 16, 1999

[54] PYRAZOLO[1,5-A]PYRIMIDINE DERIVATIVES

[75] Inventors: Makoto Inoue; Takashi Okamura; Yasuo Shoji; Kinji Hashimoto, all of Naruto; Masayuki Ohara, Tokushima-ken; Tsuneo Yasuda, Naruto, all of Japan

[73] Assignee: Otsuka Pharmaceutical Factory, Inc., Tokushima, Japan

[21] Appl. No.: 08/930,974

[22] PCT Filed: Apr. 5, 1996

[86] PCT No.: PCT/JP96/00955

§ 371 Date: Oct. 10, 1997

§ 102(e) Date: Oct. 10, 1997

[87] PCT Pub. No.: WO96/32394

PCT Pub. Date: Oct. 17, 1996

[30] Foreign Application Priority Data

Apr. 10, 1995 [JP] Japan .................................. 7-083990
Sep. 14, 1995 [JP] Japan .................................. 7-236427

[51] Int. Cl.$^6$ ...................... C07D 487/04; C07D 487/00; A61K 31/505
[52] U.S. Cl. ........................ 514/258; 544/253; 544/256; 544/255; 544/280
[58] Field of Search .................... 544/253, 256; 514/258

[56] References Cited

FOREIGN PATENT DOCUMENTS 61-57587  3/1986  Japan .
8-3167    1/1996  Japan .

OTHER PUBLICATIONS

Robins et al., (J. Heterocycl. Chem. (1985), 22 (3), pp. 601–364).
English Abstract of JP 61–57587, 1986.

*Primary Examiner*—Jose' G. Dees
*Assistant Examiner*—Sabiha N. Qazi
*Attorney, Agent, or Firm*—Sughrue, Mion, Zinn Macpeak & Seas, PLLC

[57] ABSTRACT

The invention provides pyrazolo[1,5-a]pyrimidine derivatives which are useful as potent analgesics and represented by the formula

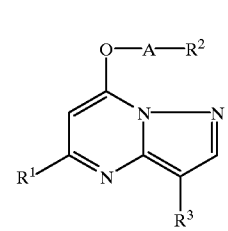

(1)

wherein $R^1$ is lower alkenyl, hydroxy(lower)alkyl, (lower)alkylthio(lower)alkyl, (lower)alkanoyloxy(lower)alkyl, (lower)alkoxy(lower)alkyl, furyl or thienyl, $R^2$ is pyridyl, 1-oxide-pyridyl, lower alkyl-substituted pyrazinyl, lower alkyl-substituted pyrimidinyl, or phenyl which may have 1 to 3 substituents selected from the group consisting of lower alkyl, lower alkoxy and halogen, $R^3$ is hydrogen or halogen, and A is a single bond or lower alkylene.

15 Claims, No Drawings

PYRAZOLO[1,5-A]PYRIMIDINE DERIVATIVES

This application is a 371 of PCT/JP96/00955 filed Apr. 5, 1996.

TECHNICAL FIELD

The present invention relates to novel pyrazolo[1,5-a]pyrimidine derivatives.

PRIOR ART

The pyrazolo[1,5-a]pyrimidine derivatives of the invention are novel compounds which have never been published in the literature.

DISCLOSURE OF THE INVENTION

An object of this invention is to provide compounds useful as medicine. The use of the compounds as medicine will be described hereinafter.

The present invention provides novel pyrazolo[1,5-a]pyrimidine derivatives represented by the following formula (1)

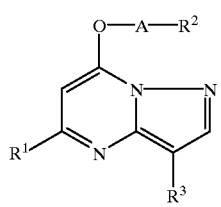

wherein $R^1$ is lower alkyl, lower alkenyl, hydroxy(lower)alkyl, (lower)alkanoyloxy(lower)alkyl, (lower)alkoxy(lower)alkyl, (lower)alkylthio(lower)alkyl, furyl or thienyl, $R^2$ is pyridyl, 1-oxide-pyridyl, lower alkyl-substituted pyrazinyl, lower alkyl-substituted pyrimidinyl, or phenyl which may have 1 to 3 substituents selected from the group consisting of lower alkyl, lower alkoxy and halogen, $R^3$ is hydrogen or halogen, and A is a single bond or lower alkylene; with the proviso that when $R^1$ is lower alkyl, $R^2$ is lower alkyl-substituted pyrazinyl or lower alkyl-substituted pyrimidinyl.

Examples of the groups in the compounds represented by the formula (1) are as follows.

The lower alkyl group includes straight- or branched-chain lower alkyl groups such as methyl, ethyl, propyl, isopropyl, butyl, isobutyl, tert-butyl, pentyl, hexyl and the like.

The lower alkenyl group includes vinyl, allyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the like.

The hydroxy(lower)alkyl group includes hydroxymethyl, 1-hydroxyethyl, 2-hydroxyethyl, 3-hydroxy-propyl, 3-hydroxybutyl, 4-hydroxybutyl, 5-hydroxypentyl, 6-hydroxyhexyl and the like.

The (lower)alkanoyloxy(lower)alkyl group includes acetoxymethyl, propionyloxymethyl, butyryloxymethyl, valeryloxymethyl, pivaloyloxymethyl, hexanoyloxymethyl, heptanoyloxymethyl, 2-acetoxyethyl, 3-acetoxypropyl, 3-acetoxybutyl, 4-acetoxybutyl, 5-acetoxypentyl, 6-acetoxyhexyl and the like.

The (lower)alkoxy(lower)alkyl group includes methoxymethyl, ethoxymethyl, propoxymethyl, isopropoxymethyl, butoxymethyl, pentyloxymethyl, hexyloxymethyl, 2-methoxyethyl, 2-ethoxyethyl, 3-methoxypropyl, 3-methoxybutyl, 4-methoxybutyl, 5-methoxypentyl, 6-methoxyhexyl and the like.

The furyl group includes 2-furyl and 3-furyl.

The thienyl group includes 2-thienyl and 3-thienyl.

The pyridyl group includes 2-pyridyl, 3-pyridyl and 4-pyridyl.

The 1-oxide-pyridyl group includes 1-oxide-2-pyridyl, 1-oxide-3-pyridyl and 1-oxide-4-pyridyl.

The halogen atom includes fluorine, chlorine, bromine and iodine.

The lower alkoxy group includes methoxy, ethoxy, propoxy, isopropoxy, butoxy, pentyloxy, hexyloxy and the like.

The (lower)alkylthio(lower)alkyl group includes methylthiomethyl, ethylthiomethyl, propylthiomethyl, butylthiomethyl, pentylthiomethyl, hexylthiomethyl, 2-methylthioethyl, 2-ethylthioethyl, 3-methylthiopropyl, 3-methylthiobutyl, 4-methylthiobutyl, 5-methylthiopentyl, 6-methylthiohexyl and the like.

The lower alkyl-substituted pyrimidinyl group includes 4-methyl-2-pyrimidinyl, 5-methyl-2-pyrimidinyl, 4,6-dimethyl-2-pyrimidinyl, 4-ethyl-2-pyrimidinyl, 5-ethyl-2-pyrimidinyl, 4,6-diethyl-2-pyrimidinyl, 4-propyl-2-pyrimidinyl, 5-propyl-2-pyrimidinyl, 4,6-dipropyl-2-pyrimidinyl, 4-butyl-2-pyrimidinyl, 5-butyl-2-pyrimidinyl, 4,6-dibutyl-2-pyrimidinyl, 4-pentyl-2-pyrimidinyl, 5-pentyl-2-pyrimidinyl, 4,6-dipentyl-2-pyrimidinyl, 4-hexyl-2-pyrimidinyl, 5-hexyl-2-pyrimidinyl, 4,6-dihexyl-2-pyrimidinyl and the like.

The lower alkyl-substituted pyrazinyl group includes 2-methyl-5-pyrazinyl, 2-methyl-3-pyrazinyl, 2-methyl-6-pyrazinyl, 2-ethyl-5-pyrazinyl, 2-propyl-5-pyrazinyl, 2-butyl-5-pyrazinyl, 2-pentyl-5-pyrazinyl, 2-hexyl-5-pyrazinyl and the like.

The lower alkylene group includes methylene, ethylene, trimethylene, tetramethylene, pentamethylene, hexamethylene and the like.

The phenyl group which may have 1 to 3 substituents selected from the group consisting of lower alkyl, lower alkoxy and halogen includes phenyl, 2-methylphenyl, 3-methylphenyl, 4-methylphenyl, 4-ethylphenyl, 4-propylphenyl, 4-butylphenyl, 4-t-butylphenyl, 4-pentylphenyl, 4-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 3,4,5-trimethoxyphenyl, 3,4,5-triethoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-dichlorophenyl, 2,4-dichlorophenyl, 3-methoxy-4-methylphenyl, 3-chloro-4-methylphenyl, 3-chloro-4-methoxyphenyl and the like.

The pyrazolo[1,5-a]pyrimidine derivatives of formula (1) according to the invention have potent analgesic effects and are useful as analgesics to relieve pains such as postoperative pain, migraine, gout, cancer pain, chronic pain and neuropathic pain. Moreover, the derivatives of the invention are free of side effects typical of conventional analgesics, do not cause hallucination or derangement and are not addictive.

The following pyrazolo[1,5-a]pyrimidine derivatives of the invention are suitable for use as analgesics: compounds of formula (1) wherein $R^1$ is lower alkyl and $R^2$ is lower alkyl-substituted pyrazinyl or lower alkyl-substituted pyrimidinyl; those wherein $R^1$ is furyl and $R^2$ is phenyl which may have 1 to 3 substituents selected from the group consisting of lower alkyl, lower alkoxy and halogen; and those wherein $R^2$ is pyridyl or 1-oxide-pyridyl and A is lower alkylene.

Of these suitable pyrazolo[1,5-a]pyrimidine derivatives, preferred are compounds of formula (1) wherein $R^1$ is lower alkenyl, $R^2$ is pyridyl or 1-oxide-pyridyl, $R^3$ is hydrogen and A is lower alkylene and those wherein $R^1$ is furyl, $R^2$ is phenyl having 1–3 lower alkoxy groups as substituents, $R^3$ is hydrogen and A is lower alkylene. The most preferable are those wherein $R^1$ is 3-butenyl or 2-furyl and A is methylene.

The most preferable pyrazolo[1,5-a]pyrimidine derivatives of the invention include 5-(3-butenyl)-7-(4-pyridylmethoxy)pyrazolo[1,5-a]pyrimidine, 4-[5-(3-butenyl)pyrazolo[1,5-a]pyrimidin-7-yl-oxymethyl] pyridine-1-oxide and 5-(2-furyl)-7-(3,4,5-trimethoxybenzyloxy)-pyrazolo[1,5-a]pyrimidine.

The derivatives of formula (1) according to the invention can be produced by various processes. Some exemplary processes are schematically shown below.

[Reaction Scheme-1]

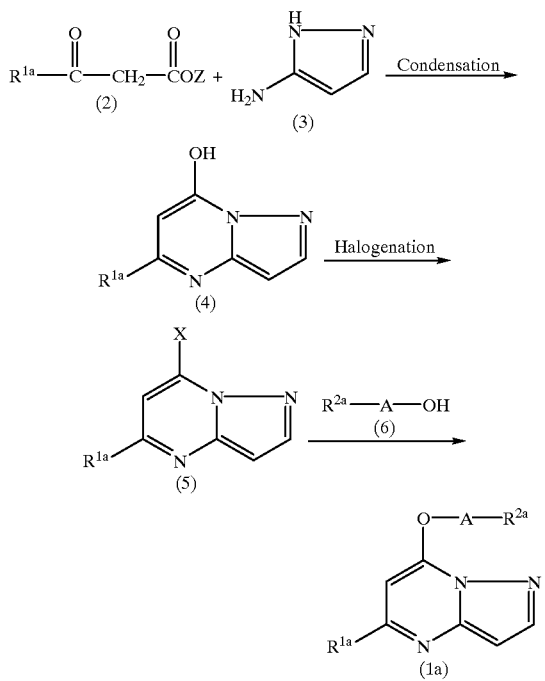

wherein A is as defined above, $R^{1a}$ is lower alkyl, lower alkenyl, (lower)alkoxy(lower)alkyl, (lower)alkylthio-(lower)alkyl, furyl or thienyl, $R^{2a}$ is pyridyl, lower alkyl-substituted pyrazinyl, lower alkyl-substituted pyrimidinyl, or phenyl which may have 1 to 3 substituents selected from the group consisting of lower alkyl, lower alkoxy and halogen, X is halogen and Z is lower alkyl; with the proviso that when $R^{1a}$ is lower alkyl, $R^{2a}$ is lower alkyl-substituted pyrazinyl or lower alkyl-substituted pyrimidinyl.

The condensation reaction of the compound (2) and 3-aminopyrazole (3) in Reaction Scheme-1 is carried out in a suitable inert solvent at a temperature ranging from room temperature to the boiling point of the solvent. Examples of useful inert solvents are acetic acid, ethanol, benzene, toluene, xylene, tetrahydrofuran (THF) and the like. The compound (2) and 3-aminopyrazole (3) are preferably used in an approximately equimolar proportion. The reaction is carried out for about 2–5 hours to provide the desired compound (4).

The subsequent halogenation reaction of the compound (4) is carried out in the presence of a suitable deacidification agent such as N,N-dimethylaniline, N,N-diethylaniline, triethylamine or the like, using a halogenating agent such as phosphorus oxychloride, phosphorus oxybromide or the like. Since the halogenating agents also function as solvents, there is no need to use other solvents in the reaction but an inert solvent such as benzene, toluene, xylene or the like may be optionally used. The deacidification agent is preferably used in an amount of about 1–10 times by weight of the compound (4). The reaction is carried out at a temperature from room temperature to about 150° C. and completed in about 0.5–12 hours.

The halide (5) obtained by the reaction is reacted with an alcohol derivative (6), giving a compound (1a) of the invention. The reaction is usually carried out in a suitable solvent in the presence of a deacidification agent.

Examples of useful deacidification agents are inorganic bases, for example, hydroxides of alkali metals such as sodium hydroxide and potassium hydroxide; bicarbonates such as sodium hydrogencarbonate; and carbonates such as potassium carbonate; and tertiary amines such as triethylamine, N,N-diethylaniline, N-methylmorpholine, pyridine and 4-dimethylaminopyridine.

Examples of useful solvents are inert solvents, for example, lower alcohols such as methanol and ethanol; chain or cyclic ethers such as tetrahydrofuran (THF) and 1,4-dioxane; and N,N-dimethylformamide (DMF) and dimethyl sulfoxide (DMSO). In the case of using an inorganic base as a deacidification agent, a mixed solvent of an inert solvent and water is preferably used. Examples of useful solvents further include aromatic hydrocarbon such as benzene, toluene, xylene and the like.

There is no limitation on the amounts of the alcohol derivative (6) and deacidification agent relative to the halide (5) in the above reaction. They are preferably used in an approximately equimolar to excessive molar amount respectively. The reaction proceeds under any of the following conditions; cooling, room temperature and heating. The reaction is usually carried out at a temperature ranging from 0° C. to reflux temperature of the solvent and completed in about 0.5–15 hours.

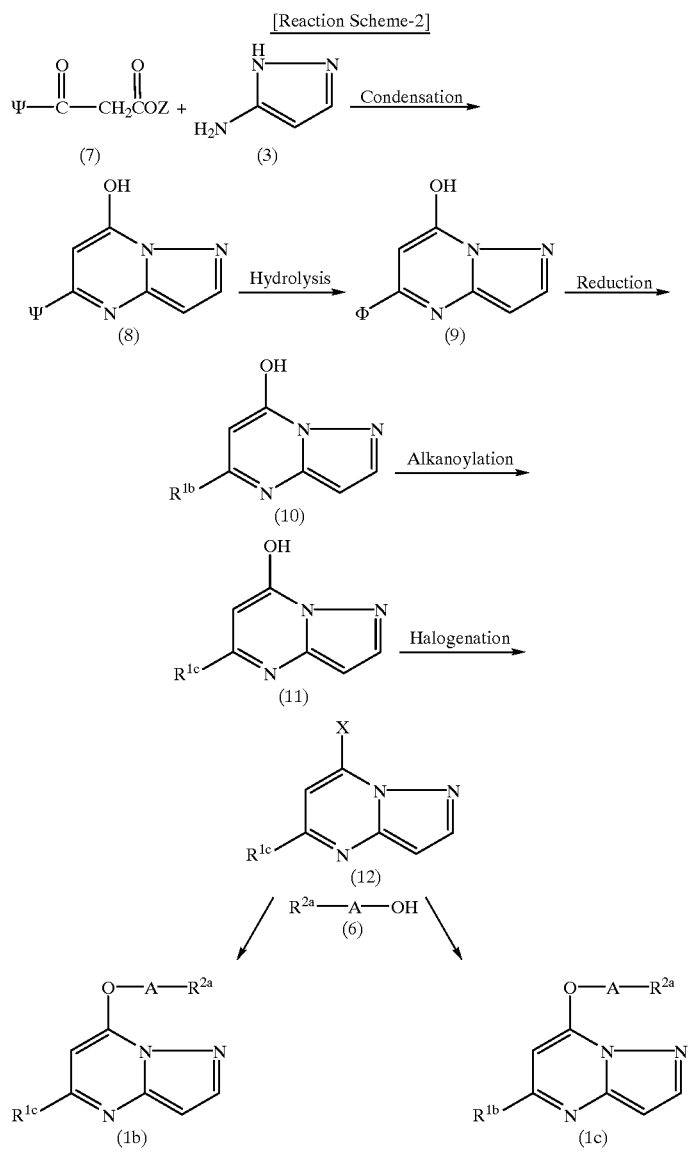

[Reaction Scheme-2]

wherein $R^{2a}$, A, X and Z are as defined above, Ψ represents lower alkyl having protected carbonyl, Φ represents lower alkyl having carbonyl, $R^{1b}$ represents hydroxy(lower)alkyl and $R^{1c}$ represents (lower)alkanoyloxy(lower)alkyl.

In Reaction Scheme-2, the condensation reaction of the compound (7) and 3-aminopyrazole derivative (3) can be carried out in a similar manner as in the reaction of the compound (2) and 3-aminopyrazole derivative (3) in Reaction Scheme-1.

Referring to "lower alkyl having protected carbonyl" represented by Ψ in the compound (7), examples are lower alkyl groups having as protected carbonyl the residue of di(lower)alkylacetal such as dimethylacetal, methylethylacetal, diethylacetal, dipropylacetal, dibutylacetal, dipentylacetal, dihexylacetal and the like and lower alkyl groups having as protected carbonyl the residue of cyclic acetal such as ethyleneacetal, trimethyleneacetal, tetramethyleneacetal and the like.

The subsequent hydrolysis reaction of the compound (8) according to Reaction Scheme-2 can be carried out using an organic acid such as acetic acid, propionic acid, p-toluenesulfonic acid or the like. Of these organic acids, carboxylic acids such as acetic acid and propionic acid can also function as solvents. When such a carboxylic acid is used, no other solvents are necessary. Even in such a case, other suitable inert solvents such as benzene, toluene, xylene or the like may be optionally used. The reaction is carried out at a temperature from room temperature to about reflux temperature of the solvent for about 10–80 hours to provide the compound (9).

The "lower alkyl having carbonyl" represented by Φ in the compound (9) includes those obtained by elimination of the protective group from the corresponding "lower alkyl having protected carbonyl" represented by Ψ. Examples are formyl, formylmethyl, acetyl, 2-formylethyl, 2-oxopropyl, propionyl, 3-formylpropyl, 3-oxobutyl, 2-oxobutyl, butyryl, 4-formylbutyl, 4-oxopentyl, 3-oxopentyl, 2-oxopentyl, valeryl, 5-formylpentyl, 5-oxohexyl, 4-oxohexyl, 3-oxohexyl, 2-oxohexyl, hexanoyl and the like.

The subsequent reduction reaction of the compound (9) is carried out using a suitable reducing agent in an inert solvent. Examples of reducing agents are borohydride compounds such as sodium borohydride, potassium borohydride, lithium borohydride, sodium cyanoborohydride, sodium triethylborohydride and the like; and lithium aluminum hydride compounds such as lithium aluminum hydride, lithium tributoxyaluminohydride and the like.

When a borohydride compound is used as a reducing agent, suitable inert solvents are alcohols such as methanol, ethanol or mixed solvents of the alcohol and another solvent such as dichloromethane, diethyl ether, etc. When a lithium aluminum hydride compound is used as a reducing agent, suitable solvents are diethyl ether, THF and like ethers. The reducing agent is preferably used in at least approximately equimolar proportion relative to the compound (9). The reaction is carried out at a temperature ranging from approximately 0° C. to room temperature for about 0.5–3 hours.

The compound (10) thus obtained is alkanoylated using an alkanoylating agent in the absence of solvents or in an inert solvent such as pyridine, lutidine, DMF or DMA. Suitable alkanoylating agents include acetic anhydride, propionic anhydride, butyric anhydride, valeric anhydride, hexanoic anhydride, heptanoic anhydride and like acid anhydrides. The alkanoylating agent is usually used in an amount of 1–10 equivalents relative to the compound (10). In order not to alkanoylate the hydroxyl group at the 7-position of the compound (10), the reaction conditions are preferably selected from a temperature range of approximately 0° C. to room temperature and a time range of about 0.5 to 2 hours.

Halogenation reaction of the compound (11) thus obtained can be carried out in a similar manner as in the reaction of the compound (4) shown in Reaction Scheme-1.

Lastly, the compound (12) thus obtained is reacted with an alcohol derivative (6) to provide the desired compounds (1b) and (1c) of the invention. This reaction can be carried out in a similar manner as in the reaction using an alcohol derivative (6) in Reaction Scheme-1. When about 1 equivalent of a deacidification agent is used in the reaction, the compound (1b) is formed as a main product. With use of a deacidification agent in an excessive amount, the compound (1c) is obtained as a main product.

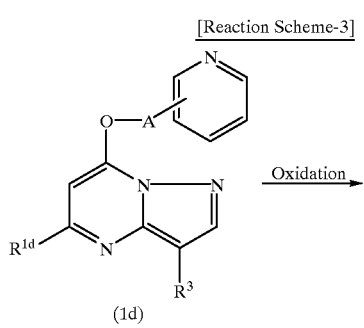

(1d)

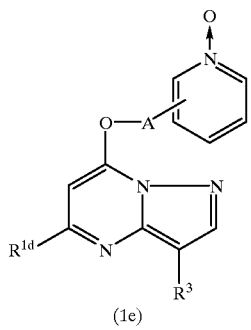

(1e)

wherein $R^{1d}$ is lower alkenyl, (lower)alkanoyloxy(lower)alkyl, (lower)alkoxy(lower)alkyl, furyl or thienyl, and $R^3$ and A are as defined above.

As shown in Reaction Scheme-3, the compound (1d) is oxidated to give a compound (1e). The oxidation can be carried out in an inert solvent such as methanol, ethanol, t-butanol, dichloromethane, chloroform, acetic acid or methanol-water and in the presence of a suitable oxidizing agent such as m-chloroperbenzoic acid, peracetic acid, aqueous hydrogen peroxide solution, or t-butylhydroperoxide. The oxidizing agent is usually used in an equimolar to slightly excessive amount relative to the compound (1d). The reaction is usually carried out at a temperature ranging from approximately 0° C. to room temperature for about 0.5–10 hours.

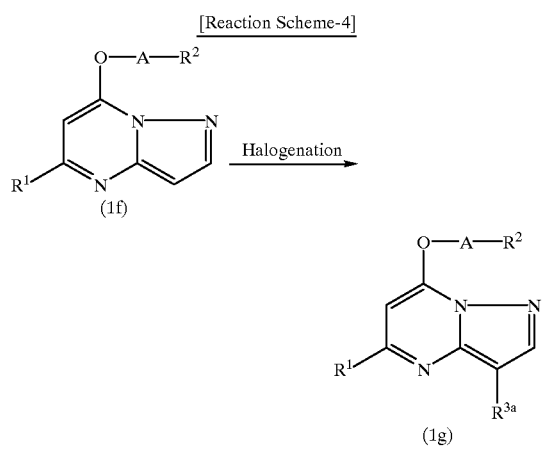

wherein $R^1$, $R^2$ and A are as defined above and $R^{3a}$ is halogen.

The halogenation reaction of the compound (1f) in Reaction Scheme-4 can be carried out using a halogenating agent such as N-bromosuccinimide (NBS), N-chlorosuccinimide (NCS) or bromine in an inert solvent such as dimethoxyethane, dimethoxyethane-water, benzene, carbon tetrachloride or the like. The halogenating agent is usually used in an amount of 1 equivalent to a slightly excessive amount relative to the compound (1f). The reaction can be carried out at a temperature ranging from approximately 0° C. to room temperature for about 0.5–5 hours.

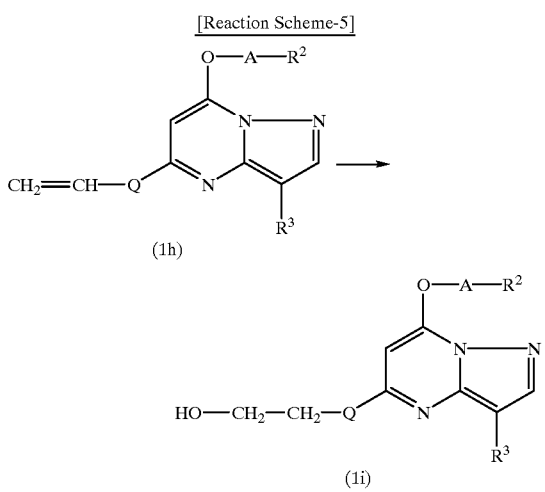

wherein $R^2$, $R^3$ and A are as defined above and Q is a single bond or $C_{1-4}$ alkylene.

The conversion reaction of compound (1h) into compound (1i) shown in Reaction Scheme-5 is carried out by hydroboration (oxidation) of the compound (1h). More specifically, the compound (1h) is reacted with 1–3 equivalents of a borohydride compound, such as diborane, borane-THF complex, borane-dimethyl amine complex, borane-methyl sulfide complex, 9-BBN (9-borabicyclo-[3,3,1] nonane) or the like in an inert solvent such as THF or diethyl ether at a temperature ranging from approximately −50° C. to room temperature for about 1 to 10 hours, and then the reaction mixture is treated with an aqueous alkali solution such as aqueous NaOH solution or aqueous KOH solution and an excess of aqueous hydrogen peroxide solution at a temperature ranging from approximately −50° C. to room temperature for about 0.5 to 5 hours.

Some compounds of the invention can be converted into pharmaceutically acceptable acid addition salts, which are also included in the scope of the invention. Examples of useful acids to form such salts are hydrochloric acid, hydrobromic acid, sulfuric acid and like inorganic acids; and oxalic acid, fumaric acid, maleic acid, tartaric acid, citric acid and like organic acids. These acid addition salts can be formed by conventional methods.

The desired compound in each of the above processes can be easily isolated by conventional separation and purification means. Useful isolation procedures include various conventional processes such as adsorption chromatography, preparative thin-layer chromatography, recrystallization, solvent extraction and the like.

Some compounds of formula (1) according to the invention may exist as optical isomers having a carbon atom as asymmetric center. The invention covers all the optical isomers (racemic derivatives, R-derivatives and S-derivatives). Also, some compounds of formula (1) according to the invention may exist as cis- or trans-isomers. The invention also covers these isomers.

The pharmaceutical compositions of the invention can be made into general dosage forms of pharmaceutical compositions using suitable pharmaceutically acceptable carrier(s).

Examples of useful pharmaceutically acceptable carriers are conventional diluents or excipients such as fillers, volume builders, binders, humectants, disintegrators, surfactants, lubricants and the like. These carriers are selectively used according to the desired unit dosage form.

The unit dosage form for the pharmaceutical compositions of the invention can be selected from a broad variety of forms according to the intended medical treatment. Typical examples are tablets, pills, powders, solutions, suspensions, emulsions, granules, capsules, suppositories, injections (solutions, suspensions, etc.), ointments and the like.

The tablets can be molded using as pharmaceutically acceptable carriers excipients such as lactose, sucrose, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, laminaran powder, sodium hydrogen-carbonate and calcium carbonate; surfactants such as polyoxyethylene sorbitan fatty acid esters, sodium lauryl sulfate and stearyl monoglyceride; disintegration inhibitors such as sucrose, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol.

Furthermore, the tablets may be optionally coated to provide sugar-coated tablets, gelatin-coated tablets, enteric tablets, film-coated tablets, etc. or be processed into double-layer or multiple-layer tablets.

The pills can be molded using as pharmaceutically acceptable carriers excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

The suppositories can be molded using as pharmaceutically acceptable carriers polyethylene glycol, cacao butter, higher alcohols or their esters, gelatin, semisynthetic glycerides and the like.

The capsules are usually manufactured by mixing an active compound of the invention with pharmaceutically acceptable carriers as mentioned above and filling the mixture into hard gelatin capsule shells, soft capsule shells, etc. according to conventional methods.

The injections in the form of solutions, emulsions, suspensions, etc. can be manufactured using diluents such as water, ethyl alcohol, macrogol, propylene glycol, ethoxylated isostearyl alcohol, polyoxylated isostearyl alcohol and polyoxyethylene sorbitan fatty acid esters. They are preferably sterilized and rendered isotonic with respect to the blood. Sodium chloride, glucose or glycerin may be incorporated in the pharmaceutical compositions of the invention in an amount sufficient to give isotonic solutions. Solubilizers, buffers, analgesics and other additives in common use may also be added.

Further, coloring agents, preservatives, fragrants, flavors, sweeteners and other medicaments may be optionally incorporated in the pharmaceutical compositions of the invention.

The ointments in the form of pastes, creams, gels, etc. can be manufactured using diluents such as white vaseline, paraffin, glycerin, cellulose derivatives, polyethylene glycol, silicone and bentonite.

The proportion of the compound of formula (1) as an active ingredient in the pharmaceutical composition of the invention is not so critical but can be selected from a broad range. Generally, it is preferable that the active ingredient accounts for about 1 to 70 weight % of the final composition.

There is no limitation on methods for administering the pharmaceutical compositions of the invention. The proper method can be determined according to the dosage form, patient's age, sex, severity of disease and other conditions. For example, the tablets, pills, solutions, suspensions, emulsions, granules and capsules are orally administered. The injections are intravenously administered singly or in admixture with a conventional replenisher such as glucose or amino acid, and optionally administered singly by the intramuscular, intradermal, subcutaneous or intraperitoneal route. The suppositories are intrarectally administered.

The dosage of the pharmaceutical composition is suitably selected according to the administration method, patient's age, sex or other conditions, severity of disease, etc. The dosage of the active ingredient compound of the invention is preferably about 0.5–20 mg per kg body weight a day and this amount can be administered once or in 2–4 divided doses a day.

BEST MODE FOR CARRYING OUT THE INVENTION

The present invention is described below in more detail with reference to Reference Examples and Examples. Reference Examples illustrate production processes for the starting compounds of the compounds of the invention. Examples illustrate production processes for the compounds of the invention.

REFERENCE EXAMPLE 1

Preparation of 5-n-butyl-7-chloropyrazolo[1,5-a]pyrimidine

Step (1)

A suspension (120 ml) of 100 g of 3-aminopyrazole and 190 g of methyl 3-oxoheptanoate in toluene was prepared and refluxed with heating at 100° C. for 3 hours. After cooling, toluene was distilled off under reduced pressure and diethyl ether was added to the residue. The crystals precipitated were collected and washed with diethyl ether and then with acetonitrile to provide 184 g of 5-n-butyl-7-hydroxypyrazolo[1,5-a]pyrimidine as colorless crystals.

Step (2)

The crystals obtained in step (1), 40 g, were added to toluene to prepare 400 ml of a suspension. Thereto were added 80 ml of phosphorus oxychloride and 44 ml of triethylamine. The mixture was refluxed with heating for 4 hours. After completion of the reaction, the reaction mixture was concentrated under reduced pressure and the residue was poured into ice water. The mixture was neutralized with sodium acetate and extracted with ethyl acetate. The organic layer was collected, washed with saturated aqueous sodium chloride solution, dried over anhydrous sodium sulfate and concentrated under reduced pressure. The residue was purified by silica gel column chromatography (eluent:ethyl acetate:n-hexane=1:9) to provide 41 g of the title compound as a light yellow oily compound.

$^1$H-NMR ($\delta$:ppm) [CDCl$_3$] 0.96 (3H, t, J=7.3), 1.4–1.5 (2H, m), 1.7–1.8 (2H, m), 2.83 (2H, t, J=7.8), 6.69 (1H, d, J=2.3), 6.86 (1H, s), 8.17 (1H, d, J=2.3)

The following compounds were prepared in a similar manner as above.

(1) 5-(3-Butenyl)-7-chloropyrazolo[1,5-a]pyrimidine

Oily compound $^1$H-NMR($\delta$: ppm) [CDCl$_3$] 2.5–2.6 (2H, m), 2.9–3.0 (2H, m), 5.0–5.1 (2H, m), 5.8–6.0 (1H, m), 6.70 (1H, d, J=2.5), 6.86 (1H, s), 8.18 (1H, d, J=2.5)

(2) 7-Chloro-5-ethoxymethylpyrazolo[1,5-a]pyrimidine

Oily compound $^1$H-NMR($\delta$: ppm) [CDCl$_3$] 1.31 (3H, t, J=6.9), 3.65 (2H, q, J=6.9), 4.63 (2H, s), 6.72 (1H, d, J=2.5), 7.22 (1H, s), 8.20 (1H, d, J=2.5)

(3) 7-Chloro-5-(2-furyl)pyrazolo[1,5-a]pyrimidine m.p.: 84–86° C.

(Recrystallization solvent: dichloromethane-n-hexane)

(4) 7-Chloro-5-(3-furyl)pyrazolo[1,5-a]pyrimidine m.p.: 143–145° C.

(Recrystallization solvent: dichloromethane-n-hexane)

(5) 7-Chloro-5-(2-thienyl)pyrazolo[1,5-a]pyrimidine m.p.: 120–122° C.

(Recrystallization solvent: dichloromethane-n-hexane)

(6) 7-Chloro-5-(3-thienyl)pyrazolo[1,5-a]pyrimidine m.p.: 123–125° C.

(Recrystallization solvent: dichloromethane-n-hexane)

(7) 7-Chloro-5-ethylthiomethylpyrazolo[1,5-a]pyrimidine Oily compound $^1$H-NMR($\delta$: ppm) [CDCl$_3$] 1.26 (3H, t, J=7.4), 2.5–2.6 (2H, q, J=7.4), 3.82 (2H, s), 6.72 (1H, d, J=2.5), 7.14 (1H, s), 8.19 (1H, d, J=2.5)

REFERENCE EXAMPLE 2

Preparation of 7-chloro-5-(3-acetoxybutyl)pyrazolo[1,5-a]pyrimidine

Step (1)

Using 0.9 g of 3-aminopyrazole and 1.9 g of methyl 2-methyl-β-oxo-1,3-dioxolane-2-valerate, the procedure of Reference Example 1 was followed. As a result, 1.85 g of 7-hydroxy-5-[2-(2-methyl-1,3-dioxolan-2-yl)ethyl]pyrazolo[1,5-a]pyrimidine was obtained as colorless crystals.

Step (2)

The compound obtained in step (1), 22 g, was dissolved in 500 ml of acetic acid-water (4:1) and stirred at 50° C. for 3 days. After completion of the reaction, the reaction mixture was concentrated under reduced pressure and the remaining acetic acid-water was azeotropically distilled off with benzene. The residue was recrystallized from ethanol-n-hexane to provide 11 g of 7-hydroxy-5-(3-oxobutyl)pyrazolo[1,5-a]pyrimidine as colorless crystals.

Step (3)

The compound obtained in step (2), 5.7 g, was dissolved in 120 ml of methanol. Sodium borohydride, 0.53 g, was added to the solution under ice-cooling. The mixture was stirred at 0° C. for 2 hours. After completion of the reaction, the reaction mixture was acidified by adding diluted hydrochloric acid dropwise and then extracted with chloroform. The organic layer was collected, washed with saturated aqueous sodium chloride solution, dried over anhydrous sodium sulfate and concentrated under reduced pressure. The residue was recrystallized from ethanol-n-hexane to provide 4.16 g of 7-hydroxy-5-(3-hydroxybutyl)pyrazolo[1,5-a]pyrimidine as colorless crystals.

Step (4)

The crystals obtained in step (3), 4.16 g, were dissolved in 40 ml of acetic anhydride and 40 ml of pyridine and stirred at room temperature for 30 minutes. After completion of the reaction, the reaction mixture was concentrated under reduced pressure and the residue was recrystallized from methanol-diethyl ether to provide 4.2 g of 5-(3-acetoxybutyl)-7-hydroxypyrazolo[1,5-a]pyrimidine as colorless crystals.

Step (5)

The compound obtained in step (4) was treated in a similar manner as in step (2) of Reference Example 1. The title compound was obtained as a light yellow oily compound.

¹H-NMR(δ: ppm) [CDCl₃] 1.30 (3H, t, J=6.4), 2.03 (3H, s), 2.0–2.1 (2H, m), 2.8–2.9 (2H, m),. 5.0–5.1 (1H, m), 6.70 (1H, d, J=2.0), 6.87 (1H, s), 8.18 (1H, d, J=2.0)

EXAMPLE 1

Preparation of 5-(3-butenyl)-7-(4-pyridylmethoxy)-pyrazolo[1,5-a]pyrimidine

60% sodium hydride, 0.55 g, was added to a 10 ml-solution of 1.6 g of 4-(hydroxymethyl)pyridine in DMF while being ice-cooled. After the mixture was stirred at 0° C. for 30 minutes, a DMF solution (2.5 ml) containing 2.6 g of 5-(3-butenyl)-7-chloropyrazolo[1,5-a]pyrimidine was added dropwise while being ice-cooled. The mixture was stirred at the same temperature for another 1 hour. After completion of the reaction, water was added to the reaction mixture. The crystals precipitated were collected by filtration and washed with water and then with diethyl ether. The crude crystals obtained were recrystallized from ethyl acetate-n-hexane to provide 1.5 g of the title compound as colorless crystals. The structure and melting point of the compound obtained are shown in Table 1.

In a similar manner as above in Example 1, the following compounds can be prepared.

5-(3-Butenyl)-7-(3-pyridylmethoxy)pyrazolo[1,5-a]pyrimidine
5-(3-Butenyl)-7-(2-pyridylmethoxy)pyrazolo[1,5-a]pyrimidine
5-(3-Butenyl)-7-(5-methylpyrazin-2-ylmethoxy)-pyrazolo[1,5-a]pyrimidine
5-(3-Butenyl)-7-(3,4,5-trimethoxybenzyloxy)-pyrazolo[1,5-a]pyrimidine
5-(3-Butenyl)-7-benzyloxypyrazolo[1,5-a]pyrimidine
5-(3-Butenyl)-7-(4-methylphenoxy)pyrazolo[1,5-a]pyrimidine
5-(3-Butenyl)-7-phenoxypyrazolo[1,5-a]pyrimidine
5-(3-Butenyl)-7-(4-chlorophenoxy)pyrazolo[1,5-a]pyrimidine
5-(3-Butenyl)-7-(3-chlorophenoxy)pyrazolo[1,5-a]pyrimidine
5-(3-Butenyl)-7-(2-chlorophenoxy)pyrazolo[1,5-a]pyrimidine
5-(3-Butenyl)-7-(2,4-dichlorophenoxy)pyrazolo-[1,5-a]pyrimidine
5-(3-Butenyl)-7-(4-chlorobenzyloxy)pyrazolo[1,5-a]pyrimidine
5-(3-Butenyl)-7-(4-methoxybenzyloxy)pyrazolo[1,5-a]pyrimidine
5-(3-Butenyl)-7-(4,6-dimethylpyrimidin-2-yloxy)-pyrazolo[1,5-a]pyrimidine
5-(3-Acetoxybutyl)-7-(3-pyridylmethoxy)pyrazolo-[1,5-a]pyrimidine
5-(3-Acetoxybutyl)-7-(2-pyridylmethoxy)pyrazolo-[1,5-a]pyrimidine
5-(3-Acetoxybutyl)-7-(5-methylpyrazin-2-yl-methoxy)pyrazolo[1,5-a]pyrimidine
5-(3-Acetoxybutyl)-7-(3,4,5-trimethoxybenzyloxy)-pyrazolo[1,5-a]pyrimidine
5-(3-Acetoxybutyl)-7-benzyloxypyrazolo[1,5-a]pyrimidine
5-(3-Acetoxybutyl)-7-(4-methylphenoxy)pyrazolo-[1,5-a]pyrimidine
5-(3-Acetoxybutyl)-7-phenoxypyrazolo[1,5-a]pyrimidine
5-(3-Acetoxybutyl)-7-(4-chlorophenoxy)pyrazolo-[1,5-a]pyrimidine
5-(3-Acetoxybutyl)-7-(3-chlorophenoxy)pyrazolo-[1,5-a]pyrimidine
5-(3-Acetoxybutyl)-7-(2-chlorophenoxy)pyrazolo-[1,5-a]pyrimidine
5-(3-Acetoxybutyl)-7-(2,4-dichlorophenoxy)-pyrazolo[1,5-a]pyrimidine
5-(3-Acetoxybutyl)-7-(4-chlorobenzyloxy)pyrazolo-[1,5-a]pyrimidine
5-(3-Acetoxybutyl)-7-(4-methoxybenzyloxy)-pyrazolo[1,5-a]pyrimidine
5-(3-Acetoxybutyl)-7-(4,6-dimethylpyrimidin-2-yloxy)pyrazolo[1,5-a]pyrimidine
5-Ethoxymethyl-7-(3-pyridylmethoxy)pyrazolo[1,5-a]pyrimidine
5-Ethoxymethyl-7-(5-methylpyrazin-2-ylmethoxy)-pyrazolo[1,5-a]pyrimidine
5-Ethoxymethyl-7-(3,4,5-trimethoxybenzyloxy)-pyrazolo[1,5-a]pyrimidine
7-Benzyloxy-5-ethoxymethylpyrazolo[1,5-a]pyrimidine
5-Ethoxymethyl-7-(4-methylphenoxy)pyrazolo[1,5-a]pyrimidine
5-Ethoxymethyl-7-phenoxypyrazolo[1,5-a]pyrimidine
7-(4-Chlorophenoxy)-5-ethoxymethylpyrazolo[1,5-a]pyrimidine
7-(3-Chlorophenoxy)-5-ethoxymethylpyrazolo[1,5-a]pyrimidine
7-(2-Chlorophenoxy)-5-ethoxymethylpyrazolo[1,5-a]pyrimidine
7-(2,4-Dichlorophenoxy)-5-ethoxymethylpyrazolo-[1,5-a]pyrimidine a
7-(4-Chlorobenzyloxy)-5-ethoxymethylpyrazolo[1,5-a]pyrimidine
5-Ethoxymethyl)-7-(4-methoxybenzyloxy)pyrazolo-[1,5-a]pyrimidine
5-Ethoxymethyl)-7-(4,6-dimethylpyrimidin-2-yl-oxy)pyrazolo[1,5-a]pyrimidine
5-Ethylthiomethyl)-7-(3-pyridylmethoxy)pyrazolo-[1,5-a]pyrimidine
5-Ethylthiomethyl)-7-(2-pyridylmethoxy)pyrazolo-[1,5-a]pyrimidine
5-Ethylthiomethyl)-7-(5-methylpyrazin-2-yl-methoxy)pyrazolo[1,5-a]pyrimidine
5-Ethylthiomethyl)-7-(3,4,5-trimethoxybenzyloxy)-pyrazolo[1,5-a]pyrimidine
7-Benzyloxy-5-ethylthiomethylpyrazolo[1,5-a]pyrimidine
5-Ethylthiomethyl-7-(4-methylphenoxy)pyrazolo-[1,5-a]pyrimidine
5-Ethylthiomethyl-7-phenoxypyrazolo[1,5-a]pyrimidine
7-(4-Chlorophenoxy)-5-ethylthiomethylpyrazolo-[1,5-a]pyrimidine
7-(3-Chlorophenoxy)-5-ethylthiomethylpyrazolo-[1,5-a]pyrimidine
7-(2-Chlorophenoxy)-5-ethylthiomethylpyrazolo-pyrazolo[1,5-a]pyrimidine
7-(2,4-Dichlorophenoxy)-5-ethylthiomethyl-pyrazolo[1,5-a]pyrimidine
7-(4-Chlorobenzyloxy)-5-ethylthiomethylpyrazolo-[1,5-a]pyrimidine
5-Ethylthiomethyl-7-(4-methoxybenzyloxy)pyrazolo-[1,5-a]pyrimnidine
5-Ethylthiomethyl-7-(4,6-dimethylpyrimidin-2-yloxy)pyrazolo[1,5-a]pyrimidine
5-(2-Furyl)-7-(5-methylpyrazin-2-ylmethoxy)-pyrazolo[1,5-a]pyrimidine
5-(3-Furyl)-7-(5-methylpyrazin-2-ylmethoxy)-pyrazolo[1,5-a]pyrimidine
7-(5-Methylpyrazin-2-ylmethoxy)-5-(2-thienyl)-pyrazolo[1,5-a]pyrimidine
7-(5-Methylpyrazin-2-ylmethoxy)-5-(3-thienyl)-pyrazolo[1,5-a]pyrimidine
5-(2-Furyl)-7-(4,6-dimethylpyrimidin-2-yloxy)-pyrazolo[1,5-a]pyrimidine
5-(3-Furyl)-7-(4,6-dimethylpyrimidin-2-yloxy)-pyrazolo[1,5-a]pyrimidine 7-(4,6-Dimethylpyrimidin-2-yloxy)-5-(2-thienyl)-pyrazolo [1,5-a]pyrimidine 7-(4,6-Dimethylpyrimidin-2-yloxy)-5-(3-thienyl)-pyrazolo [1,5-a]pyrimidine

EXAMPLES 2–18

The compounds set forth in Table 1 were prepared in a similar manner as in Example 1. Table 1 shows the structure and melting points of the compounds obtained.

EXAMPLE 19

Preparation of 5-(3-hydroxybutyl)-7-(4-pyridylmethoxy)-pyrazolo[1,5-a]pyrimidine The procedure of Example 1 was followed except using 340 mg of 4-(hydroxymethyl)pyridine, 280 mg of 5-(3-acetoxybutyl)-7-chloropyrazolo[1,5-a]pyrimidine and 105 mg of 60% sodium hydride and using DMF as a solvent. The title compound was obtained as colorless crystals (50 mg). The structure and melting point of the compound obtained are shown in Table 1.

The following compounds can be prepared in a similar manner as above in Example 19.

5-(3-Hydroxybutyl)-7-(3-pyridylmethoxy)pyrazolo-[1,5-a]pyrimidine 5-(3-Hydroxybutyl)-7-(2-pyridylmethoxy)pyrazolo-[1,5-a]pyrimidine 5-(3-Hydroxybutyl)-7-(5-methylpyrazin-2-yl-methoxy)pyrazolo[1,5-a]pyrimidine 5-(3-Hydroxybutyl)-7-(3,4,5-trimethoxybenzyloxy)-pyrazolo[1,5-a]pyrimidine 7-Benzyloxy-5-(3-hydroxybutyl)pyrazolo[1,5-a]pyrimidine 5-(3-Hydroxybutyl)-7-(4-methylphenoxy)pyrazolo-[1,5-a]pyrimidine 5-(3-Hydroxybutyl)-7-phenoxypyrazolo[1,5-a]pyrimidine 7-(4-Chlorophenoxy)-5-(3-hydroxybutyl)pyrazolo-[1,5-a]pyrimidine 7-(3-Chlorophenoxy)-5-(3-hydroxybutyl)pyrazolo-[1,5-a]pyrimidine 7-(2-Chlorophenoxy)-5-(3-hydroxybutyl)pyrazolo-[1,5-a]pyrimidine 7-(2,4-Dichlorophenoxy)-5-(3-hydroxybutyl)-pyrazolo[1,5-a]pyrimidine 7-(4-Chlorobenzyloxy)-5-(3-hydroxybutyl)pyrazolo-[1,5-a]pyrimidine 5-(3-Hydroxybutyl)-7-(4-methoxybenzyloxy)-pyrazolo[1,5-a]pyrimidine 5-(3-Hydroxybutyl)-7-(4,6-dimethylpyrimidin-2-yloxy)pyrazolo[1,5-a]pyrimidine

EXAMPLE 20

Preparation of 4-[5-(3-butenyl)pyrazolo[1,5-a]pyrimidin-7-yloxymethyl]pyridine-1-oxide 5-(3-Butenyl)-7-(4-pyridylmethoxy)pyrazolo[1,5-a]pyrimidine (compound of Example 1), 500 mg, was dissolved in dichloromethane to provide 5 ml of a solution. Thereto was added 660 mg of 70% m-chloroperbenzoic acid. The mixture was stirred at 0° C. for 1 hour. After completion of the reaction, saturated aqueous sodium bicarbonate solution was added and the mixture was extracted with chloroform. The organic layer was collected, washed in sequence with water and saturated aqueous sodium chloride solution, dried over anhydrous sodium sulfate and concentrated under reduced pressure. The residue was purified by silica gel column chromatography (eluent: chloroform:methanol=10:1) and recrystallized from ethyl acetate-n-hexane to provide 110 mg of the title compound as colorless crystals. The structure and melting point of the compound obtained are shown in Table 1.

The following compounds can be prepared in a similar manner as above in Example 20.

4-[5-(3-Acetoxybutyl)pyrazolo[1,5-a]pyrimidin-7-yloxymethyl]pyridine-1-oxide

4-[5-(Ethoxymethyl)pyrazolo[1,5-a]pyrimidin-7-yloxymethyl]pyridine-1-oxide

2-[5-(Ethoxymethyl)pyrazolo[1,5-a]pyrimidin-7-yloxymethyl]pyridine-1-oxide

4-[5-(2-furyl)pyrazolo[1,5-a]pyrimidin-7-yloxymethyl]pyridine-1-oxide

3-[5-(2-furyl)pyrazolo[1,5-a]pyrimidin-7-yloxymethyl]pyridine-1-oxide

2-[5-(2-furyl)pyrazolo[1,5-a]pyrimidin-7-yloxymethyl]pyridine-1-oxide

4-[5-(3-furyl)pyrazolo[1,5-a]pyrimidin-7-yloxymethyl]pyridine-1-oxide

4-[5-(2-thienyl)pyrazolo[1,5-a]pyrimidin-7-yloxymethyl]pyridine-1-oxide

4-[5-(3-thienyl)pyrazolo[1,5-a]pyrimidin-7-yloxymethyl]pyridine-1-oxide

EXAMPLE 21

Preparation of 3-bromo-5-(3-butenyl)-7-(4-pyridylmethoxy)pyrazolo[1,5-a]pyrimidine 5-(3-Butenyl)-7-(4-pyridylmethoxy)pyrazolo[1,5-a]pyrimidine (compound of Example 1), 500 mg, was dissolved in 10 ml of dimethoxyethane-water (3:1). The solution was cooled to 0° C. and 380 mg of NBS was added. The mixture was stirred at 0° C. for 1 hour and further stirred at room temperature for 1 hour. Water was added to the reaction mixture and the crystals precipitated were collected by filtration. The crude crystals were recrystallized from dichloromethane-n-hexane to provide 440 mg of the title compound as colorless crystals. The structure and melting point of the compound obtained are shown in Table 1.

The following compounds can be prepared in a similar manner as above in Example 21.

5-(3-Acetoxybutyl)-3-bromo-7-(4-pyridylmethoxy)-pyrazolo[1,5-a]pyrimidine

3-Bromo-5-butyl-7-(5-methylpyrazin-2-ylmethoxy)-pyrazolo[1,5-a]pyrimidine

3-Bromo-5-ethoxymethyl-7-(4-pyridylmethoxy)-pyrazolo[1,5-a]pyrimidine

3-Bromo-5-ethoxymethyl-7-(2-pyridylmethoxy)-pyrazolo[1,5-a]pyrimidine

3-Bromo-5-(2-furyl)-7-(4-pyridylmethoxy)pyrazolo-[1,5-a]pyrimidine

3-Bromo-5-(2-furyl)-7-(3-pyridylmethoxy)pyrazolo-[1,5-a]pyrimidine

3-Bromo-5-(2-furyl)-7-(2-pyridylmethoxy)pyrazolo-[1,5-a]pyrimidine

3-Bromo-5-(2-furyl)-7-(3,4,5-trimethoxybenzyl-oxy)pyrazolo[1,5-a]pyrimidine

7-Benzyloxy-3-bromo-5-(2-furyl)pyrazolo[1,5-a]pyrimidine

3-Bromo-5-(2-furyl)-7-(4-methylphenoxy)pyrazolo-[1,5-a]pyrimidine

3-Bromo-5-(2-furyl)-7-phenoxypyrazolo[1,5-a]pyrimidine

3-Bromo-7-(4-chlorophenoxy)-5-(2-furyl)pyrazolo-[1,5-a]pyrimidine

3-Bromo-5-(3-furyl)-7-(4-pyridylmethoxy)pyrazolo-[1,5-a]pyrimidine

3-Bromo-7-(4-pyridylmethoxy)-5-(2-thienyl)-pyrazolo[1,5-a]pyrimidine

3-Bromo-7-(4-pyridylmethoxy)-5-(3-thienyl)-pyrazolo[1,5-a]pyrimidine

3-Bromo-7-(4-chlorobenzyloxy)-5-(2-furyl)-pyrazolo[1,5-a]pyrimidine

3-Bromo-7-(4-methoxybenzyloxy)-5-(2-furyl)-pyrazolo[1,5-a]pyrimidine

3-Bromo-5-(3-hydroxybutyl)-7-(4-pyridylmethoxy)-pyrazolo[1,5-a]pyrimidine

4-[3-bromo-5-(3-butenyl)pyrazolo[1,5-a]pyrimidin-7-yloxymethyl]pyridine-1-oxide

3-Bromo-5-(4-hydroxybutyl)-7-(4-pyridylmethoxy)-pyrazolo[1,5-a]pyrimidine

3-Bromo-7-(2-chlorophenoxy)-5-(2-furyl)pyrazolo-[1,5-a]pyrimidine

3-Bromo-7-(3-chlorophenoxy)-5-(2-furyl)pyrazolo-[1,5-a]pyrimidine

3-Bromo-7-(2,4-dichlorophenoxy)-5-(2-furyl)-pyrazolo[1,5-a]pyrimidine

3-Bromo-5-(2-furyl)-7-(4,6-dimethylpyrimidin-2-yloxy)pyrazolo[1,5-a]pyrimidine

3-Bromo-7-(4-chlorophenoxy)-5-(2-thienyl)-pyrazolo[1,5-a]pyrimidine

3-Bromo-5-ethylthiomethyl-7-(4-pyridylmethoxy)-pyrazolo[1,5-a]pyrimidine

EXAMPLE 22

Preparation of 5-(4-hydroxybutyl)-7-(4-pyridylmethoxy)-pyrazolo[5-a]pyrimidine 5-(3-Butenyl)-7-(4-pyridylmethoxy)pyrazolo[1,5-a]pyrimidine (compound of Example 1), 300 mg, was dissolved in 3.0 ml of anhydrous THF. Thereto were added dropwise 4.3 ml of a THF solution containing 0.5M of 9-BBN in a stream of argon at 0° C. The mixture was stirred at 0° C. for 1 hour and further stirred at room temperature for 1 hour. Thereto were added 0.5 ml of water and 0.6 ml of aqueous 3M NaOH solution in sequence. The mixture was stirred at room temperature for 1 hour. Lastly 0.6 ml of 30% aqueous hydrogen peroxide solution was added and the mixture was stirred at room temperature for 1 hour. The reaction mixture was extracted with chloroform. The organic layer was collected, washed in sequence with water and saturated aqueous sodium chloride solution, dried over anhydrous sodium sulfate and concentrated under reduced pressure. The residue was purified by silica gel column chromatography (eluent: chloroform:methanol=20:1) and recrystallized from chloroform-ethyl acetate to provide 70 mg of the title compound as colorless crystals. The structure and melting point of the compound obtained are shown in Table 1.

In a similar manner as above in Example 22, the following compounds can be prepared using the compounds of the present invention wherein $R^1$ is lower alkenyl (3-butenyl).

5-(4-hydroxybutyl)-7-(3-pyridylmethoxy)pyrazolo-[1,5-a]pyrimidine 5-(4-hydroxybutyl)-7-(2-pyridylmethoxy)pyrazolo-[1,5-a]pyrimidine 5-(4-hydroxybutyl)-7-(5-methylpyrazin-2-yl-methoxy)pyrazolo[1,5-a]pyrimidine 5-(4-hydroxybutyl)-7-(3,4,5-trimethoxybenzyloxy)pyrazolo[1,5-a]pyrimidine 7-benzyloxy-5-(4-hydroxybutyl)pyrazolo[1,5-a]pyrimidine 5-(4-hydroxybutyl)-7-(4-methylphenoxy)pyrazolo-[1,5-a]pyrimidine 5-(4-hydroxybutyl)-7-phenoxypyrazolo[1,5-a]pyrimidine 7-(4-chlorophenoxy)-5-(4-hydroxybutyl)pyrazolo-[1,5-a]pyrimidine 7-(3-chlorophenoxy)-5-(4-hydroxybutyl)pyrazolo-[1,5-a]pyrimidine 7-(2-chlorophenoxy)-5-(4-hydroxybutyl)pyrazolo-[1,5-a]pyrimidine 7-(2,4-dichlorophenoxy)-5-(4-hydroxybutyl)-pyrazolo[1,5-a]pyrimidine 7-(4-chlorobenzyloxy)-5-(4-hydroxybutyl)pyrazolo-[1,5-a]pyrimidine 5-(4-hydroxybutyl)-7-(4-methoxybenzyloxy)-pyrazolo[1,5-a]pyrimidine 5-(4-hydroxybutyl)-7-(4,6-dimethylpyrimidin-2-yloxy)pyrazolo[1,5-a]pyrimidine

EXAMPLES 23–28

The compounds set forth in Table 1 were prepared in a similar manner as in Example 1. Table 1 shows the structure and melting points of the compounds obtained.

TABLE 1

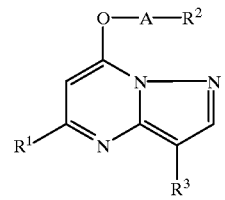

Me: Methyl group, Et: Ethyl group, nBu: N-Butyl group,
Ph: Phenyl group, Ac: Acetyl group

| Ex. No. | $R^1$ | $R^2$ | $R^3$ | A | Melting Point (° C.) (Recrystallization solvent) |
|---|---|---|---|---|---|
| 1 | $CH_2{=}CH{-}CH_2{-}CH_2{-}$ | 4-pyridyl | H | $CH_2$ | 159~161 (Ethyl acetate-n-hexane) |
| 2 | $CH_3{-}CH(OAc){-}CH_2{-}CH_2{-}$ | 4-pyridyl | H | $CH_2$ | 113~115 (Ethyl acetate-n-hexane) |

TABLE 1-continued

[Structure: pyrazolo[1,5-a]pyrimidine with O-A-R² at one position, R¹ and R³ substituents]

Me: Methyl group, Et: Ethyl group, nBu: N-Butyl group,
Ph: Phenyl group, Ac: Acetyl group

| Ex. No. | R¹ | R² | R³ | A | Melting Point (° C.) (Recrystallization solvent) |
|---|---|---|---|---|---|
| 3 | nBu | 5-methyl-pyrazin-2-yl (Me-pyrazine) | H | CH₂ | 124~126 (Dichloromethane-n-hexane) |
| 4 | EtOCH₂— | pyridin-4-yl | H | CH₂ | 132~134 (Dichloromethane-diethyl ether) |
| 5 | EtOCH₂— | pyridin-2-yl | H | CH₂ | 89~92 (Dichloromethane-diethyl ether) |
| 6 | 2-furyl | pyridin-4-yl | H | CH₂ | 169~171 (Ethyl acetate-n-hexane) |
| 7 | 2-furyl | pyridin-2-yl | H | CH₂ | 164~166 (Ethyl acetate-n-hexane) |
| 8 | 2-furyl | pyridin-3-yl | H | CH₂ | 156~158 (Ethyl acetate-n-hexane) |
| 9 | 2-furyl | 3,4,5-trimethoxy-phenyl | H | CH₂ | 136~138 (Ethyl acetate-n-hexane) |
| 10 | 2-furyl | Ph | H | CH₂ | 174~176 (Ethyl acetate-n-hexane) |
| 11 | 2-furyl | 4-methylphenyl | H | S.B. | 157~159 (Ethyl acetate-n-hexane) |
| 12 | 2-furyl | Ph | H | S.B. | 131~133 (Ethyl acetate-n-hexane) |

TABLE 1-continued

Structure:
$$\text{R}^1\text{-substituted pyrazolo[1,5-a]pyrimidine with O-A-R}^2 \text{ at 7-position and R}^3 \text{ at 3-position}$$

Me: Methyl group, Et: Ethyl group, nBu: N-Butyl group,
Ph: Phenyl group, Ac: Acetyl group

| Ex. No. | R¹ | R² | R³ | A | Melting Point (° C.) (Recrystallization solvent) |
|---|---|---|---|---|---|
| 13 | 2-furyl | 4-chlorophenyl | H | S.B. | 148~150 (Ethyl acetate-n-hexane) |
| 14 | 2-furyl | 4-pyridyl | H | CH₂ | 180~182 (Ethyl acetate-n-hexane) |
| 15 | 2-thienyl | 4-pyridyl | H | CH₂ | 174~176 (Ethyl acetate-n-hexane) |
| 16 | 3-thienyl | 4-pyridyl | H | CH₂ | 160~162 (Ethyl acetate-n-hexane) |
| 17 | 2-furyl | 4-chlorophenyl | H | CH₂ | 127~129 (Ethyl acetate-n-hexane) |
| 18 | 2-furyl | 4-methoxyphenyl | H | CH₂ | 124~126 (Ethyl acetate-n-hexane) |
| 19 | $CH_3-CH(OH)-CH_2-CH_2-$ | 4-pyridyl | H | CH₂ | 125~127 (Ethyl acetate-n-hexane) |
| 20 | $CH_2=CH-CH_2-CH_2-$ | 4-pyridyl N-oxide | H | CH₂ | 129~131 (Ethyl acetate-n-hexane) |
| 21 | $CH_2=CH-CH_2-CH_2-$ | 4-pyridyl | Br | CH₂ | 117~119 (Dichloromethane-diethyl eter) |
| 22 | $HO-CH_2CH_2-CH_2CH_2-$ | 4-pyridyl | H | CH₂ | 162~164 (Chloroform-ethyl acetate) |

TABLE 1-continued

[Structure: pyrazolo[1,5-a]pyrimidine core with O—A—R² at 7-position, R¹ at 5-position, R³ at 3-position]

Me: Methyl group, Et: Ethyl group, nBu: N-Butyl group,
Ph: Phenyl group, Ac: Acetyl group

| Ex. No. | R¹ | R² | R³ | A | Melting Point (° C.) (Recrystallization solvent) |
|---|---|---|---|---|---|
| 23 | 2-furyl | 2-chlorophenyl | H | S.B. | 132~134 (Diethyl ether-n-hexane) |
| 24 | 2-furyl | 3-chlorophenyl | H | S.B. | 112~114 (Diethyl ether-n-hexane) |
| 25 | 2-furyl | 3,4-dichlorophenyl | H | S.B. | 150~152 (Diethyl ether-n-hexane) |
| 26 | nBu | 2,6-dimethylpyrimidin-4-yl | H | S.B. | 68~70 (n-Hexane) |
| 27 | 2-thienyl | 4-chlorophenyl | H | S.B. | 116~118 (Diethyl ether-n-hexane) |
| 28 | EtSCH₂— | pyridin-4-yl | H | CH₂ | 107~109 (Ethyl acetate-n-hexane) |

*In column A. "SB" means "Single bond".

Pharmacological Test Example 1

Using 6-week-old male Wistar rats (n=7/group), the pain threshold of each rat's left hind paw was determined using Analgesy-Meter (Unicom) in accordance with the Randall-Selitto method [Randall, L. O. and Selitto, J. J., Arch. Int. Pharmacodyn., 111, 409 (1957)]. The value thus obtained was termed "pre-value".

One hour after measurement of the pre-value, 0.1 ml of a 20% yeast suspension was subcutaneously injected into the left hind paw of each rat. Immediately after the yeast injection, a 5% gum arabic suspension containing the compound of the invention was orally administered to the rats of the test group in an amount of 10 ml/kg, whereas a 5% gum arabic suspension (not containing the compound of the invention) was administered likewise to the rats of the control group.

The pain threshold of each rats left hind paw was determined in the same manner as above at an interval of exactly one hour from the time of the yeast injection. The value thus obtained was termed "Post-value".

The recovery (%) of the pain threshold was calculated from post-values and pre-values of the rats in each group, by means of the following formula.

Recovery of pain threshold (%)=

$$\frac{\text{(Test group average post-value)} - \text{(Control group average post-value)}}{\text{(Control group average pre-value)} - \text{(Control group average post-value)}} \times 100$$

The results (the highest recovery %) are shown in Table 2.

TABLE 2

| Example No. | Recovery (%) | Dosage (mg/kg) | Time from yeast injection (hr. later) |
| --- | --- | --- | --- |
| 1 | 65.3 | 10 | 4 |
| 4 | 69.3 | 3 | 1 |
| 9 | 75.4 | 3 | 3 |
| 13 | 102.9 | 3 | 4 |
| 19 | 47.9 | 1 | 3 |

Pharmacological Test Example 2

Using 6-week-old male Wistar rats (n=7/group), the pain threshold of each rat's left hind paw was determined using Analgesy-Meter (Unicom) in accordance with the Randall-Selitto method [Randall, L. O. and Selitto J. J., Arch. Int. Pharmacodyn., 111, 409 (1957)]. The value thus obtained was termed "pre-value".

One hour after measurement of the pre-value, a 5% gum arabic suspension containing the compound of the invention was orally administered to the rats of the test group in an amount of 10 ml/kg so that the dosage of the compound of the invention was 1 mg/kg, whereas a 5% gum arabic suspension (not containing the compound of the invention) was administered likewise to the rats of the control group. One hour later, an aqueous physiological saline solution containing substance P (25 ng/0.1 ml) was subcutaneously injected into the left hind paw of each rat.

The pain threshold of each rat's left hind paw was determined in the same manner as above at a predetermined interval from the time of the substance P injection. The value thus obtained was termed "post-value".

The recovery (%) of the pain threshold was calculated from post-values and pre-values of the rats in each group, by means of the following formula.

$$\frac{\text{(Test group average post-value)} - \text{(Control group average post-value)}}{\text{(Control group average pre-value)} - \text{(Control group average post-value)}} \times 100$$

The results (the highest recovery %) are shown in Table 3.

TABLE 3

| Example No. | Recovery (%) | Time from substance P injection (minutes later) |
| --- | --- | --- |
| 1 | 118.6 | 30 |
| 4 | 100.7 | 15 |
| 5 | 73.4 | 60 |
| 6 | 52.0 | 60 |
| 9 | 60.3 | 60 |
| 13 | 63.6 | 60 |
| 14 | 56.2 | 60 |
| 16 | 56.8 | 30 |
| 18 | 33.1 | 30 |
| 20 | 89.2 | 60 |
| 22 | 45.4 | 60 |
| 23 | 34.9 | 30 |
| 25 | 52.3 | 60 |
| 26 | 43.5 | 60 |
| 28 | 52.9 | 30 |

Given below are Formulation Examples for manufacturing analgesic compositions of the invention.

Formulation Example 1

Manufacture of tablets

Tablets (1000 tables) for oral administration, each containing 5 mg of the compound obtained in Example 1, were manufactured according to the following formula:

| | |
| --- | --- |
| Compound of Example 1 | 5 g |
| Lactose (Japanese pharmacopoeia: JP) | 50 g |
| Corn starch (JP) | 25 g |
| Crystalline cellulose (JP) | 25 g |
| Methyl cellulose (JP) | 1.5 g |
| Magnesium stearate (JP) | 1 g |

More specifically, the compound of Example 1, lactose, corn starch and crystalline cellulose were fully blended and granulated using a 5% aqueous methyl cellulose solution. The granulated mixture was passed through a 200-mesh sieve and dried carefully. The dried granules were passed through a 200-mesh sieve, and the granules under the sieve were mixed with magnesium stearate and compression-molded into tablets.

Formulation Example 2

Manufacture of capsules

Two-piece hard gelatin capsules (1000 units) for oral administration, each containing 10 mg of the compound obtained in Example 9, were manufactured according to the following formula:

| | |
| --- | --- |
| Compound of Example 9 | 10 g |
| Lactose (JP) | 80 g |
| Corn starch (JP) | 30 g |
| Talc (JP) | 5 g |
| Magnesium stearate (JP) | 1 g |

More specifically, the above ingredients were finely pulverized and blended to give a homogeneous composition. This composition was filled into propersized capsule shells for oral administration.

Industrial Applicability

The pyrazolo[1,5-a]pyrimidine derivatives according to the present invention have potent analgesic effects and are useful as analgesics.

What is claimed is:

1. A pyrazolo[1,5-a]pyrimidine derivative of the formula

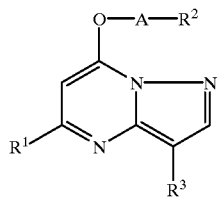

(1)

wherein $R^1$ is lower alkenyl, hydroxy(lower)alkyl, (lower)alkanoyloxy(lower)alkyl, (lower)alkoxy(lower)alkyl, (lower)alkylthio(lower)alkyl, furyl or thienyl, $R^2$ is pyridyl, 1-oxide-pyridyl, lower alkyl-substituted pyrazinyl, lower alkyl-substituted pyrimidinyl, or phenyl which may have 1 to 3 substituents selected from the group consisting of lower alkyl, lower alkoxy and halogen, $R^3$ is hydrogen or halogen, and A is a single bond or lower alkylene.

2. A pyrazolo[1,5-a]pyrimidine derivative according to claim 1, which is selected from the group consisting of the compounds of formula (1) wherein $R^1$ is furyl and $R^2$ is phenyl which may have 1 to 3 substituents selected from the group consisting of lower alkyl, lower alkoxy and halogen, and those wherein $R^2$ is pyridyl or 1-oxide-pyridyl and A is lower alkylene.

3. A pyrazolo[1,5-a]pyrimidine derivative according to claim 2, which is selected from the group consisting of the compounds wherein $R^1$ is lower alkenyl, $R^2$ is pyridyl or 1-oxide-pyridyl, $R^3$ is hydrogen and A is lower alkylene and the compounds wherein $R^1$ is furyl and $R^2$ is phenyl which may have 1 to 3 lower alkoxy groups, $R^3$ is hydrogen and A is lower alkylene.

4. A pyrazolo[1,5-a]pyrimidine derivative according to claim 3 wherein $R^1$ is 3-butenyl or 2-furyl and A is methylene.

5. A pyrazolo[1,5-a]pyrimidine derivative according to claim 4, which is selected from the group consisting of 5-(3-butenyl)-7-(4-pyridylmethoxy)pyrazolo[1,5-a]pyrimidine, 4-[5-(3-butenyl)pyrazolo[1,5-a]pyrimidin-7-yloxymethyl]pyridine-1-oxide and 5-(2-furyl)-7-(3,4,5-trimethoxybenzyloxy)pyrazolo[1,5-a]pyrimidine.

6. An analgesic composition which comprises an effective amount of a pyrazolo[1,5-a]pyrimidine derivative defined in one of claims 1–5 and a pharmaceutically acceptable carrier.

7. A method for relieving pain, which comprises administering to a patient an effective amount of a pyrazolo[1,5-a]pyrimidine derivative of the formula

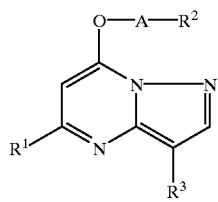

(1)

wherein $R^1$ is lower alkenyl, hydroxy(lower)alkyl, (lower)alkanoyloxy(lower)alkyl, (lower)alkoxy(lower)alkyl, (lower)alkylthio(lower)alkyl, furyl or thienyl, $R^2$ is pyridyl, 1-oxide-pyridyl, lower alkyl-substituted pyrazinyl, lower alkyl-substituted pyrimidinyl, or phenyl which may have 1 to 3 substituents selected from the group consisting of lower alkyl, lower alkoxy and halogen, $R^3$ is hydrogen or halogen, and A is a single bond or lower alkylene.

8. The method according to claim 7, wherein the pyrazolo[1,5-a]pyrimidine derivative is selected from the group consisting of the compounds of formula (1) wherein (a) $R^1$ is furyl and $R^2$ is phenyl optionally having 1 to 3 substituents selected from the group consisting of lower alkyl, lower alkoxy and halogen, and (b) $R^2$ is pyridyl or 1-oxide-pyridyl and A is lower alkylene.

9. The method according to claim 7, wherein the pyrazolo[1,5-a]pyrimidine derivative is selected from the group consisting of the compounds of formula (1) wherein (a) $R^1$ is lower alkenyl, $R^2$ is pyridyl or 1-oxide-pyridyl, $R^3$ is hydrogen and A is lower alkenylene and (b) $R^1$ is furyl and $R^2$ is phenyl optionally having 1 to 3 lower alkoxy groups, $R^3$ is hydrogen and A is lower alkylene.

10. The method according to claim 7, wherein $R^1$ is 3-butenyl or 2-furyl and A is methylene.

11. The method according to claim 7, wherein the pyrazolo[1,5-a]pyrimidine derivative is selected from the group consisting of 5-(3-butenyl)-7-(4-pyridylmethoxy)pyrazolo[1,5-a]pyrimidine, 4-[5-(3-butenyl)pyrazolo[1,5-a]pyrimidin-7-yloxymethyl]pyridine-1-oxide and 5-(2-furyl)-7-(3,4,5-trimethoxy-benzyloxy)pyrazolo[1,5-a]pyrimidine.

12. The method according to claim 7, wherein the method of administering the pyrazolo[1,5-a]pyrimidine derivative to said patient is oral, intravenous, intramuscular, intradermal, subcutaneous, intra-peritoneal, or intrarectal administering.

13. A pharmaceutical composition suitable for use as a pain reliever comprising the pyrazolo[1,5-a]pyrimidine derivative of claim 1 and at least one pharmaceutically acceptable carrier.

14. The pharmaceutical composition according to claim 13, wherein the composition is in a dosage form selected from the group consisting of tablets, pills, powders, solutions, suspensions, emulsions, granules, capsules, suppositories, injections and ointments.

15. A unit dose of the pyrazolo[1,5-a]pyrimidine derivative of claim 1, wherein the unit dose is about 0.125–20 mg per kg body weight of a patient to whom the dose is administered.

* * * * *